United States Patent [19]

Yamada et al.

[11] Patent Number: 4,564,638
[45] Date of Patent: Jan. 14, 1986

[54] FUNGICIDAL NOVEL N-BENZYL-N-(2-NORBORNYL)-UREAS

[75] Inventors: Yasuo Yamada, Hino; Junichi Saito, Mitaka; Tatsuo Tamura, Hamura; Shinji Sakawa, Hino, all of Japan

[73] Assignee: Nihon Tokushu Boyaku Seizo K.K., Tokyo, Japan

[21] Appl. No.: 503,212

[22] Filed: Jun. 10, 1983

[30] Foreign Application Priority Data

Jun. 17, 1982 [JP] Japan ................. 57-103004

[51] Int. Cl.[4] ................. A01N 47/32; C07C 157/05; C07C 127/15
[52] U.S. Cl. ................. 514/585; 514/587; 514/596; 564/26; 564/28; 564/29; 564/52; 564/53; 564/54; 564/56
[58] Field of Search ................. 564/56, 54, 53, 52, 564/28, 26, 29; 424/322; 71/120; 514/585, 587, 596

[56] References Cited

U.S. PATENT DOCUMENTS

- 3,174,843  3/1965  Buntin et al. .
- 3,304,167  2/1967  Buntin et al. .
- 4,127,673  11/1978  Yamada et al. ............. 424/322
- 4,216,228  8/1980  Yamada et al. ............. 564/26

FOREIGN PATENT DOCUMENTS

- 0000376  1/1979  European Pat. Off. .
- 0072528  2/1983  European Pat. Off. ............. 564/56
- 2359123  2/1978  France .

*Primary Examiner*—Charles F. Warren
*Assistant Examiner*—Carolyn S. Greason
*Attorney, Agent, or Firm*—Sprung Horn Kramer & Woods

[57] ABSTRACT

Fungicidally active novel benzylurea derivatives of the formula

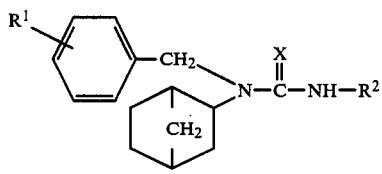

in which
  $R^1$ is a halogen atom or a lower alkyl group,
  X is an oxygen or sulfur atom, and
  $R^2$ is an alkyl group, a cycloalkyl group having 5 to 8 carbon atoms, or a phenyl group which may be substituted by at least one member of the class consisting of halogen atoms, lower alkyl groups, lower alkoxy groups and hydroxyl groups.

11 Claims, No Drawings

FUNGICIDAL NOVEL N-BENZYL-N-(2-NORBORNYL)-UREAS

DETAILED DESCRIPTION OF THE INVENTION

This invention relates to a novel benzylurea derivative, a process for production thereof, and an agricultural and horticultural fungicide.

More specifically, this invention relates to a benzylurea derivative of general formula (I)

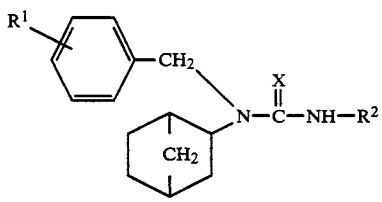

(I)

wherein
$R^1$ represents a halogen atom or a lower alkyl group,
X represents an oxygen or sulfur atom, and
$R^2$ represents an alkyl group, a cycloalkyl group having 5 to 8 carbon atoms, or a phenyl group which may be substituted by at least one member of the class consisting of halogen atoms, lower alkyl groups, lower alkoxy groups and hydroxyl groups.

The compound of general formula (I) can be produced by the following processes to which this invention also pertains.

PROCESS (I)

A process for producing the benzylurea derivative of general formula (I), which comprises reacting an amine represented by the general formula

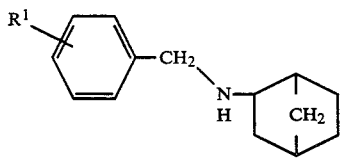

(II)

wherein $R^1$ is as defined hereinabove, with an isocyanate represented by the general formula $$R^2-N=C=X \qquad (III)$$

wherein X and $R^2$ are as defined hereinabove.

PROCESS (II)

A process for producing the benzylurea derivative of general formula (I), which comprises reacting a carbamoyl halide represented by the general formula

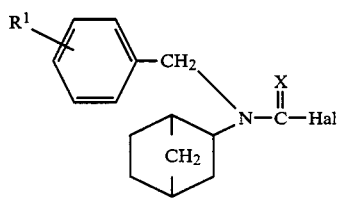

(IV)

wherein $R^1$ and X are as defined hereinabove, with an amine represented by the general formula $$H_2N-R^2 \qquad (V)$$

wherein $R^2$ is as defined hereinabove.

This invention also pertains to an agricultural and horticultural fungicide comprising the benzylurea derivative of general formula (I) as an active ingredient.

The present inventors made extensive investigations in order to create novel compounds having fungicidal activity. These investigations have now led to the discovery that the benzylurea derivatives of general formula (I) given hereinabove are novel compounds not described in the known literature, and have excellent fungicidal activity for agriculture and horticulture.

It has been found by the work of the present inventors that the compounds of formula (I) exhibit an excellent control effect against sheat blight (*Pellicularia sasakii*), which is the most important disease like blast (*Piricularia oryzae* Cavara) in controlling fungi in rice cultivation by stalk and foliar spraying treatment or water surface treatment.

It has also been found that the compounds of this invention exhibit an excellent control effect not observed heretofore by their excellent penetrating and migrating ability when they are applied to a water surface. Accordingly, the compounds of this invention have a great industrial merit in saving the work required in performing water surface treatment.

It has further been found that the compounds of this invention exhibit an excellent control effect against damping-off of vegatables caused by *Rhizoctonia solani* which has been a problem in recent years.

The characteristics of the compounds of this invention reside not only in a biological aspect but also in their chemical structure. Specifically, the compounds of this invention are characterized, as shown by general formula (I), by the fact that they have a urea or thiourea structure as a basic skeleton, and this basic structure has a substituted benzyl group at the 1-position nitrogen atom, a lower alkyl group, a cycloalkyl group having 5 to 8 carbon atoms or a substituted phenyl group at the 3-position nitrogen atom, and as the greatest characteristic feature of the compounds of this invention, a norbornyl group further at the 1-position nitrogen atom.

The present inventors have found that the compounds of this invention having such a unique structure and not described in the known literature can be easily synthesized, and owing to such a novel chemical structure, they have outstanding fungicidal activity.

It is an object of this invention therefore to provide the novel benzylurea derivatives of general formula (I), processes for production thereof, and their use as an agricultural and horticultural fungicide.

The above and other objects and advantages of this invention will become more apparent from the following description.

The active compounds of this invention can be used against pathogenic fungi parasitic on the terrestrial parts of plants, pathogenic fungi which attack plants from the soil and cause tracheomycosis, seed-spreading pathogenic fungi, and soil-spreading pathogenic fungi.

Furthermore, since these compounds are characterized by having low toxicity to warm-blooded animals and good affinity for higher plants, namely having no phytotoxicity to cultivated plants in usual dosages, they can be quite conveniently used as agricultural and horticultural chemicals to control plant diseases caused by pathogenic fungi.

As fungicides, the compounds of formula (I) of this invention can be effectively used to control various fungus diseases caused by Archimycetes, Phycomycetes, Ascomycetes, Basidiomycetes, and *Fungi Imperfecti*, and other bacteria.

The benzylurea derivatives of the invention represented by general formula (I) can be produced by the following processes (i) and (ii).

PROCESS (I)

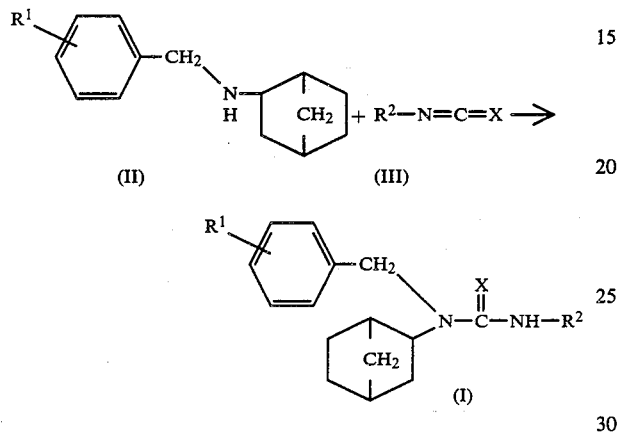

In the formulae, R¹, X and R² are the same as defined hereinabove.

Specific examples of R¹ are halogen atoms such as fluorine, chlorine, bromine and iodine, and lower alkyl groups having 1 to 4 carbon atoms such as methyl, ethyl, propyl, isopropyl and n-(iso-, sec-, or tert-)butyl group.

X represents an oxygen or sulfur atom.

Specific examples of R² include lower alkyl groups having 1 to 4 carbon atoms as exemplified hereinabove, alkyl groups having 5 to 8 carbon atoms such as n-(or iso-)pentyl, n-(or iso-)hexyl, n-heptyl and n-octyl, cycloalkyl groups having 5 to 8 carbon atoms such as cyclopentyl, cyclohexyl, cycloheptyl and cyclooctyl, and a phenyl group which may be substituted by at least one member selected from the class consisting of the same halogen atoms as exemplified above, the same lower alkyl groups having 1 to 4 carbon atoms as exemplified above, lower alkoxy groups having the same lower alkyl groups as exemplified hereinabove, and hydroxyl groups.

Specific examples of the amine of general formula (II) as a starting material in the process for producing the compounds of this invention shown by the above reaction scheme include N-4-chlorobenzyl-2-norbornylamine,
N-4-bromobenzyl-2-norbornylamine, and
N-4-methylbenzyl-2-norbornylamine.

Specific examples of the isocyanate of general formula (III) which is likewise a starting material include
methyl isocyanate,
ethyl isocyanate,
propyl isocyanate,
isopropyl isocyanate,
n-butyl isocyanate,
n-hexyl isocyanate,
cyclopentyl isocyanate,
cyclohexyl isocyanate,
phenyl isocyanate,
2-chlorophenyl isocyanate,
4-chlorophenyl isocyanate,
4-hydroxyphenyl isocyanate,
o-tolyl isocyanate,
p-tolyl isocyanate,
3-methoxyphenyl isocyanate,
methyl isothiocyanate,
ethyl isothiocyanate,
n-butyl isothiocyanate,
phenyl isothiocyanate, and
cyclohexyl isothiocyanate.

By citing a typical example, the above process will be described specifically.

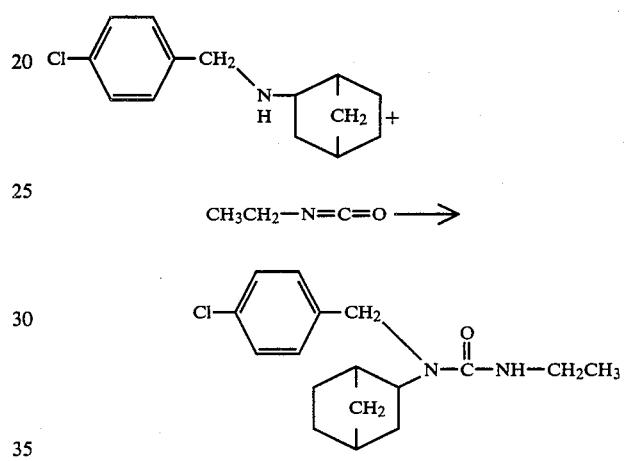

The above process can be carried out desirably by using a solvent or diluent. For this purpose, all inert solvents and diluents can be used.

Examples of such solvents or diluents are water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-iso-propyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile, and acrylonitrile; esters such as ethyl acetate and amyl acetate; acid amides such as dimethylformamide and dimethylacetamide; sulfones and sulfoxides, such as dimethyl sulfoxide and sulfolane; and bases such as pyridine.

This process of this invention can be carried out over a wide temperature range, generally at a temperature between about −20° C. and the boiling point of the mixture, desirably at a temperature between about 0° and about 100° C. Desirably, the reaction is carried out under normal atmospheric pressure, but it is also possible to operate under elevated or reduced pressures.

Compounds of general formula (I) in which R² is a hydroxy-substituted phenyl group are preferably produced by the process (i).

PROCESS (II)

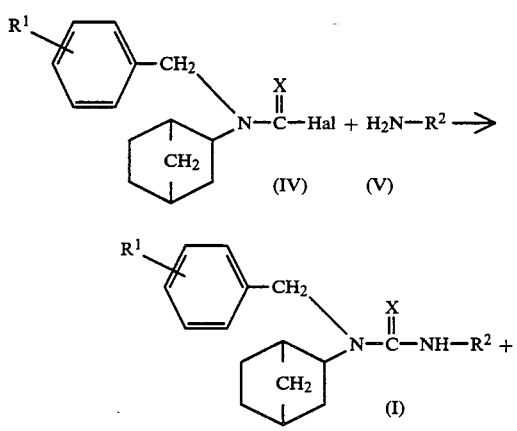

In the above formulae, $R^1$, X, $R^2$ and Hal are as defined above.

In the reaction scheme, specific examples of $R^1$, X and $R^2$ are the same as those exemplified hereinabove. Specific examples of Hal are the same halogen atoms as described above, preferably chlorine and bromine.

In the process shown by the above reaction scheme, specific examples of the carbamoyl halide of general formula (IV) as a starting material include
N-4-chlorobenzyl-N-2-norbornylcarbamoyl chloride,
N-4-bronobenzyl-N-2-norbornylcarbamoyl chloride,
N-4-methylbenzyl-N-2-norbornylcarbamoyl chloride,
N-4-chlorobenzyl-N-2-norbornylthiocarbamoyl chloride,
N-4-bronobenzyl-N-2-norbornylthiocarbamoyl chloride, and
N-4-methylbenzyl-N-2-norbornylthiocarbamoyl chloride.
The corresponding bromides may also be cited.

Specific examples of the amine of general formula (V) which is likewise a starting material include
methylamine,
ethylamine,
propylamine,
isopropylamine,
n-butylamine,
n-hexylamine,
cyclopentylamine,
cyclohexylamine,
aniline,
2-chloroaniline,
4-chloroaniline,
4-hydroxyaniline,
o-toluidine,
p-toluidine, and
3-methoxyaniline.

By citing a typical example, the process (ii) will be described specifically.

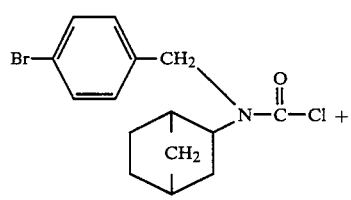

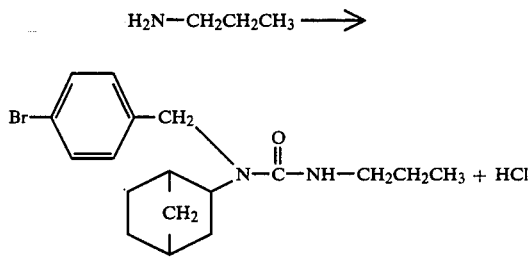

The process (ii) can be performed by using the same inert solvent or diluent as exemplified hereinabove to give the desired product in high purity and yield.

The above reaction can be carried out in the presence of an acid binder. Examples of such an acid binder are the hydroxides, carbonates, bicarbonates and alcoholates of alkali metals, and tertiary amines such as triethylamine, diethylaniline and pyridine, all of which are normally used.

The above process can be carried out over a wide temperature range, generally at a temperature between about $-20°$ C. and the boiling point of the mixture, desirably at a temperature between about $0°$ and about $100°$ C. The reaction is desirably carried out under normal atmospheric pressure, but it is also possible to operate under elevated or reduced pressures.

For use as an agricultural or horticultural fungicide, the compound of this invention may be used as such after diluting it directly with water, or formulating it into various forms using agriculturally acceptable adjuvants by methods generally practiced in the production of agricultural chemicals. In actual use, the compositions in various forms are applied either directly or after diluting them with water to the desired concentrations.

Examples of the agriculturally acceptable adjuvants, as referred to herein, are diluents (solvents, extenders, carriers), surface-active agents (solubilizing agents, emulsifiers, dispersants, wetting agents), stabilizers, stickers, aerosol propellants, and synergists.

Examples of the solvents are water, and organic solvents, for example hydrocarbons [e.g., n-hexane, petroleum ether, naphtha, petroleum fractions (e.g., paraffin waxes, kerosene, light oils, middle oils, heavy oils), benzene, toluene, and xylenes], halogenated hydrocarbons [e.g., methylene chloride, carbon tetrachloride, trichloroethylene, ethylene chloride, ethylene dibromide, chlorobenzene and chloroform], alcohols [e.g., methyl alcohol, ethyl alcohol, propyl alcohol, and ethylene glycol], ethers [e.g., ethyl ether, ethylene oxide and dioxane], alcohol ethers [e.g., ethylene glycol monomethyl ether], ketones [e.g., acetone and isophorone], esters [e.g., ethyl acetate and amyl acetate], amides [e.g., dimethylformamide and dimethylacetamide] and sulfoxides [e.g., dimethyl sulfoxide].

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (e.g., pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfuric acid esters (e.g., sodium laurylsulfate), arylsulfonic acid salts (e.g., alkyl-arylsulfonic acid salts and sodium alkylnaphthalenesulfonates), succinic acid salts and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (e.g., agicultural soaps, casein lime, sodium alginate, polyvinyl alcohol, vinyl acetate-type adhesives and acrylic adhesives); aerosol propellants (e.g., trichlorofluoromethane, dichlorofluoromethane, 1,2,2-trichloro-1,1,2-trifluoroethane, chlorobenzene, LNG and lower ethers); combustion controlling agents for fumigants (e.g., nitrites, zinc powder and dicyandiamide); oxygen supplying agents (e.g., chloric acid salts, and bichromic acid salts); effect-prolonging agents; dispersion stabilizers (e.g., casein, tragacanth, carboxymethyl cellulose and polyvinyl alcohol); and synergists.

The compounds of this invention can be formulated into various forms by methods generally practiced in the field of manufacturing agricultural chemicals. Examples of the forms include emulsifiable concentrates, oils, wettable powders, soluble powders, suspensions, dusts, granules, pulverulent compositions, fumigants, tablets, aerosols, pastes and capsules.

The agricultural and horticultural fungicide of this invention may contain about 0.1 to about 95% by weight, preferably about 0.5 to about 90% by weight, of the active ingredient.

In actual use, the suitable amount of the active compound in the aforesaid compositions in various forms and ready-to-use preparations is, for example, about 0.0001 to about 20% by weight, preferably about 0.005 to about 10% by weight.

The content of the active ingredient can be properly varied depending upon the form of the preparation or composition, the method, purpose, time and locus of its application, the state of occurrence of plant diseases, etc.

If required, the compound of this invention may be used further in combination with other agricultural chemicals, for example insecticides, other fungicides, miticides, nematocides, antiviral agents, herbicides, plant growth regulators and attractants [e.g., organophosphorus ester compounds, carbamate compounds, dithio (or thiol)carbamate compounds, organic chlorine compounds, dinitro compounds, organic sulfur or metal compounds, antibiotics, substituted diphenyl ether compounds, urea compounds, and triazine compounds], and/or fertilizers.

Various compositions and ready-to-use preparations containing the aforesaid active ingredient can be applied by various methods generally practiced in the field of agricultural chemical application, for example spraying (such as liquid spraying, misting, atomizing, dusting, granule scattering, water surface application, and pouring); fumigation; soil application (such as mixing, sprinkling, vaporing, and injecting); surface application (such as coating, banding, dust coating, and covering); and dipping. They can also be used by the so-called ultralow volume spraying method. According to this method, the active ingredient can be included in an amount of 100%.

The rate of application per unit area is, for example, about 0.03 to about 10 kg, preferably about 0.3 to about 6 kg, per hectare. In special cases, however, it may, and sometimes should, be outside the specified range.

According to this invention, there can be provided an agricultural and horticultural fungicidal composition comprising the compound of general formula (I) as an active ingredient and a diluent (a solvent and/or an extender and/or a carrier) and/or a surface-active agent, and if further required, a stabilizer, a sticker, a synergist, etc.

The invention also provides a method for controlling a plant disease, which comprises applying to a pathogenic fungus, and/or the locus where said fungus or a disease thereby occurs the compound of general formula (I) alone or in admixture with a diluent (a solvent and/or an extender and/or a carrier) and/or a surface active agent and if required, a stabilizer, a sticker, a synergist, etc.

The following examples illustrate the present invention specifically. It should be noted however that the invention is not limited to these specific examples alone.

EXAMPLE 1

Wettable powder

Fifteen parts of compound No. 1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto a pathogenic fungus and/or the locus where the fungus or a disease thereby occurs.

EXAMPLE 2

Emulsifiable concentrate

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto a pathogenic fungus and/or the locus where the fungus or a disease thereby occurs.

EXAMPLE 3

Dust

Two parts of compound No. 3 of the invention and 98 parts of powdery clay are pulverized and mixed to form a dust. It is scattered over a pathogenic fungus and/or the locus where the fungus or a disease thereby occurs.

EXAMPLE 4

Dust

Compound No. 4 of the invention (1.5 parts), 0.5 part of isopropyl hydrogen phosphate, and 98 parts of powdery clay are pulverized and mixed to form a dust. It is scattered over a pathogenic fungus and/or the locus where the fungus or a disease thereby occurs.

EXAMPLE 5

Granules

Water (25 parts) is added to a mixture consisting of 10 parts of compound No. 5 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over a pathogenic fungus and/or the locus where the fungus or a disease thereby occurs.

EXAMPLE 6

Granules

Ninety-five parts of clay mineral particles having a particle size distribution of 0.2 to 2 mm are put in a rotary mixer, and with rotation, 5 parts of compound No. 6 of the invention dissolved in an organic solvent is sprayed uniformly over the clay mineral particles. The clay mineral particles are then dried at 40° to 50° C. to form granules. The granules are scattered over a pathogenic fungus and/or the locus where the fungus or a disease thereby occurs.

EXAMPLE 7

Oil

Compound No. 7 of the invention (0.5 part) and 99.5 parts of kerosene are mixed with stirring to form an oil. It is sprayed onto a pathogenic fungus and/or the locus where the fungus or a disease thereby occurs.

The excellent fungicidal effect of the active compounds of this invention can be observed from the results of the following test examples.

TEST EXAMPLE 1

Test for a control effect against sheath blight (Pellicularia sasakii) (pot test)

Preparation of a test chemical:
Active compound: 50 parts by weight
Carrier: 45 parts by weight of a mixture (1:5) of diatomaceous earth and kaolin
Emulsifier: 5 parts by weight of polyoxyethylene alkyl phenyl ether The active compound, the carrier and the emulsifier in the amounts indicated above were mixed to form a wettable powder. A predetermined amount of the wettable powder was diluted with water to form a test chemical.

Testing method
Rice (variety: Kinmaze) was cultivated in Wagner pots (1/5,000 are) in a watered state. In the young ear forming stage, a dilution of the test chemical prepared as above in a predetermined concentration was sprayed at a rate of 100 ml per three pots. On the next day after the spraying, a fungus causing sheath blight (Pellicularia sasakii) cultivated for 10 days in a barley medium until sclerotia were formed were inoculated in the bottom of the rice plant hill. The rice plant was kept for 10 days in a chamber maintained at a temperature of 28° to 30° C. and a relative humidity of at least 95% to induce sheath blight. Then, the degree of the disease and the occurrence of phytotoxicity were examined. The degree of injury was expressed by the following standard on the basis of the extension of a lesion from the inoculated part of the roots.

$$\text{Degree of injury} = \frac{3n_3 + 2n_2 + n_1 + n_o}{3N} \times 100$$

wherein
N: the total number of stalks examined,
$n_o$: the number of stalks not infected by the disease
$n_1$: the number of stalks which were diseased up to a sheath of the first leaf (from the bottom),
$n_2$: the number of stalks which were diseased up to a sheath of the second leaf; and
$n_3$: the number of stalks which were diseased up to a sheath of the third leaf.

The results are shown in Table 1.

TABLE 1

| Compound No. | Concentration of the active ingredient (ppm) | Degree of injury (%) | Phytotoxicity |
|---|---|---|---|
| 1 | 25 | 0 | — |
| 2 | 125 | 0 | — |
| 3 | 25 | 0 | — |
| 4 | 25 | 0 | — |
| 5 | 25 | 0 | — |
| 7 | 25 | 0 | — |
| 8 | 25 | 0 | — |
| 11 | 125 | 0 | — |
| 13 | 125 | 0 | — |
| 14 | 125 | 0 | — |
| 15 | 250 | 0 | — |
| 17 | 25 | 0 | — |
| 18 | 125 | 0 | — |
| 19 | 25 | 0 | — |
| 20 | 25 | 0 | — |
| 21 | 25 | 0 | — |
| 22 | 250 | 0 | — |
| 23 | 25 | 0 | — |
| 24 | 25 | 0 | — |
| 25 | 25 | 0 | — |
| 26 | 25 | 0 | — |
| 27 | 25 | 0 | — |
| 28 | 250 | 0 | — |
| Polyoxin (Commercial product used as a control) | 45 | 21.5 | — |
| Validamycin A (Commercial product used as a control) | 60 | 10 | — |

Note
1 The compound numbers in the table correspond to those in Synthesis Examples and Table 4 hereinbelow.
2 Polyoxin: Polyoxin compound zinc salt
3 Validamycin A: 3% liquid preparation of Validamycin A.
4 The symbol "—" in the column of phytotoxicity in the table shows that there was no phytotoxicity.

TEST EXAMPLE 2

Test for the effect of water surface application in controlling rice sheath blight Testing method:
Three stocks of rice (variety: Nihonbare) were planted in a white porcelain pot having a diameter of 12 cm, and cultivated in a watered condition. In the initial period of their tillering stage, a preparation of the test chemical formed in a predetermined concentration in the same way as in Test Example 1 was injected onto the water surface to the indicated amount by means of a pipette so that the test chemical did not splash over the terrestrial part of the rice directly. Five days later, of the desired 1-(4-chlorobenzyl)-1-(2-norbornyl)-3-phenylurea. mp. 111°–113° C.

Compounds of this invention synthesized by substantially the same methods as in Synthesis Examples 1 and 2 are shown in Table 4.

TABLE 4

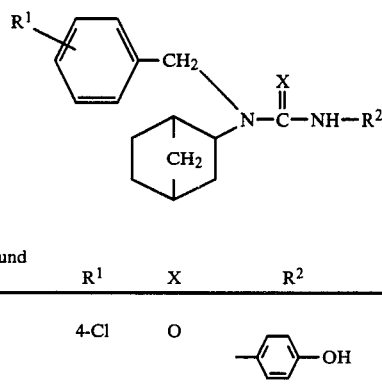

| Compound No. | $R^1$ | X | $R^2$ | Physical constant (mp, °C.) |
|---|---|---|---|---|
| 2 | 4-Cl | O | —CH$_3$ | 121–123 |
| 3 | 4-Cl | O | n-C$_3$H$_7$ | 95–96 |
| 4 | 4-Cl | O | iso-C$_3$H$_7$ | 125–126 |
| 5 | 4-Cl | O | n-C$_4$H$_9$ | 88–89 |
| 6 | 4-Cl | O | n-C$_6$H$_{13}$ | 86–87 |
| 7 | 4-Cl | O | cyclopentyl | 98–99 |
| 8 | 4-Cl | O | cyclohexyl | 115–117 |
| 9 | 4-Cl | O | 2-Cl-phenyl | 111–113 |
| 10 | 4-Cl | O | 4-Cl-phenyl | 151–153 |
| 11 | 4-Cl | O | 2-CH$_3$-phenyl | 133–134 |
| 12 | 4-Cl | O | 4-CH$_3$-phenyl | 127–129 |
| 13 | 4-Cl | O | 2-OCH$_3$-phenyl | 126–127 |
| 14 | 4-Br | O | —CH$_3$ | 136–137 |
| 15 | 4-Br | O | n-C$_3$H$_7$ | 80–81 |
| 16 | 4-Br | O | n-C$_6$H$_{13}$ | 76–78 |
| 17 | 4-Cl | S | —CH$_3$ | 124–125 |
| 18 | 4-Cl | S | —C$_2$H$_5$ | 70–73 |
| 20 | 4-Br | O | phenyl | 132–133 |
| 21 | 4-CH$_3$ | O | —C$_2$H$_5$ | 98–99 |
| 22 | 4-CH$_3$ | O | n-C$_3$H$_7$ | 74–75 |
| 23 | 4-CH$_3$ | O | n-C$_4$H$_9$ | 49–52 |
| 24 | 4-CH$_3$ | O | cyclohexyl | 89–90 |
| 25 | 4-CH$_3$ | O | phenyl | 121–122 |
| 26 | 4-Cl | S | n-C$_4$H$_9$ | 99–101 |
| 27 | 4-Br | S | —CH$_3$ | 119–120 |

TABLE 4-continued

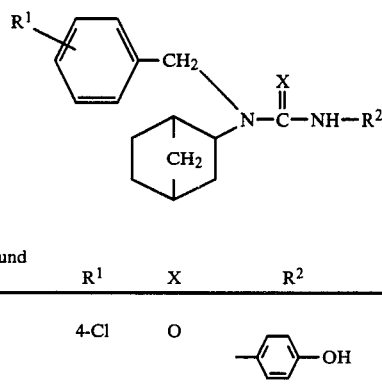

| Compound No. | $R^1$ | X | $R^2$ | Physical constant (mp, °C.) |
|---|---|---|---|---|
| 28 | 4-Cl | O | 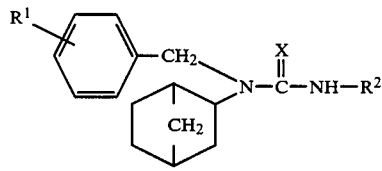 | 178–180 |

It will be appreciated that the instant specification and examples are set forth by way of illustration and not limitation, and that various modifications and changes may be made without departing from the spirit and scope of the present invention.

What is claimed is:

1. A benzylurea derivative of by the formula

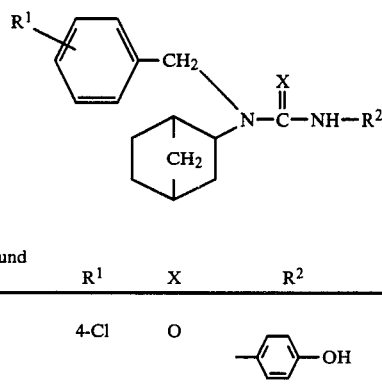

in which
   $R^1$ is a halogen atom or a lower alkyl group,
   X is an oxygen or sulfur atom, and
   $R^2$ is an alkyl group, a cycloalkyl group having 5 to 8 carbon atoms, or a phenyl group which may be substituted by at least one member of the class consisting of halogen atoms, lower alkyl groups, lower alkoxy groups and hydroxyl groups.

2. A compound according to claim 1, in which
   $R^1$ is chloro, bromo or methyl, and
   $R^2$ is an alkyl group having 1 to 4 carbon atoms, a cycloalkyl group having 5 to 8 carbon atoms, a phenyl group, or a phenyl group substituted by a halogen atom, an alkyl or alkoxy group having 1 to 4 carbon atoms and/or a hydroxyl group.

3. A compound according to claim 2, in which
   $R^1$ is in the para-position, and
   X is oxygen.

4. A compound according to claim 1, wherein such compound is 1-(4-chlorobenzyl)-3-ethyl-1-(2-norbornyl)urea of the formula

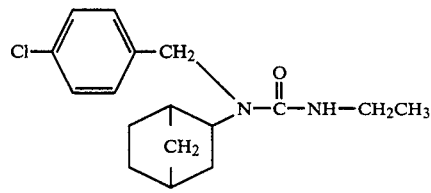

5. A compound according to claim 1, wherein such compound is 1-(4-chlorobenzyl)-1-(2-norbornyl)-3-phenylurea of the formula

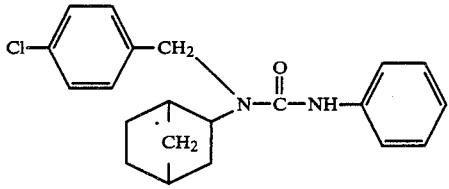

6. A compound according to claim 1, wherein such compound is 1-(4-bromobenzyl)-1-(2-norbornyl)-3-propylurea of the formula

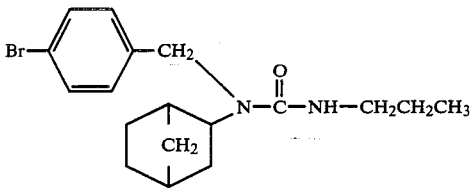

7. A compound according to claim 1, wherein such compound is 1-(4-chlorobenzyl-3-ethyl-1-(2-norbornyl)thiourea of the formula

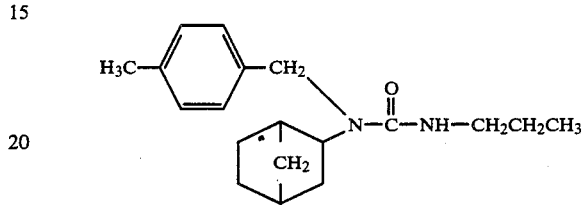

8. A compound according to claim 1, wherein such compound is 1-(4-methylbenzyl)-1-(2-norbornyl)-3-propylurea of the formula 9. A fungicidal composition comprising a fungicidally effect amount of a compound according to claim 1 in admixture with a diluent.

10. A method of combating fungi which comprises applying to such fungi or to a fungi habitat a fungicidally effective amount of a compound according to claim 1.

11. The method according to claim 10, wherein such compound is
1-(4-chlorobenzyl)-3-ethyl-1-(2-norbornyl)urea,
1-(4-chlorobenzyl)-1-(2-norbornyl)-3-phenylurea,
1-(4-bromobenzyl)-1-(2-norbornyl)-3-propylurea,
1-(4-chlorobenzyl-3-ethyl-1-(2-norbornyl)thiourea, or
1-(4-methylbenzyl)-1-(2-norbornyl)-3-propylureau.

* * * * *

UNITED STATES PATENT AND TRADEMARK OFFICE
CERTIFICATE OF CORRECTION

PATENT NO. : 4,564,638

DATED : January 14, 1986

INVENTOR(S) : Yasuo Yamada, et al.

It is certified that error appears in the above-identified patent and that said Letters Patent is hereby corrected as shown below:

Col. 1, line 35 and
 Col. 3, line 11      Delete "Process (I)" and substitute --Process (i)--
Col. 1, line 55 and
 Col. 5, line 1       Delete "Process (II)" and substitute --Process (ii)--
Col. 2, line 19       Correct spelling of "sheath"
Col. 16, line 26      Delete "effect" and substitute --effective--

Signed and Sealed this

Twentieth Day of May 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,564,638
DATED : January 14, 1986
INVENTOR(S) : YASUO YAMADA et al It is certified that error appears in the above—identified patent and that said Letters Patent is hereby corrected as shown below:

Title page, No. 73 "Assignee", delete "Boyaku" and insert therefor -- Noyaku --.

Signed and Sealed this

Twelfth Day of August 1986

[SEAL]

Attest:

DONALD J. QUIGG

Attesting Officer

Commissioner of Patents and Trademarks